United States Patent
Lean et al.

(10) Patent No.: US 7,811,438 B2
(45) Date of Patent: Oct. 12, 2010

(54) BIO-ENRICHMENT DEVICE TO ENHANCE SAMPLE COLLECTION AND DETECTION

(75) Inventors: Meng H. Lean, Santa Clara, CA (US); Armin R. Völkel, Mountain View, CA (US); Peter Kiesel, Palo Alto, CA (US); Oliver Schmidt, Palo Alto, CA (US); Noble M. Johnson, Menlo Park, CA (US); H. Ben Hsieh, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 892 days.

(21) Appl. No.: 11/007,121

(22) Filed: Dec. 8, 2004

(65) Prior Publication Data
US 2006/0121555 A1    Jun. 8, 2006

(51) Int. Cl.
B03C 5/02    (2006.01)

(52) U.S. Cl. ............... 204/643; 204/450; 204/600; 204/645

(58) Field of Classification Search ............ 204/547, 204/450, 456, 466, 600–674; 209/156, 208, 209/210, 209, 12; 210/748.01
See application file for complete search history.

(56) References Cited

U.S. PATENT DOCUMENTS

| | | |
|---|---|---|
| 3,449,938 A | 6/1969 | Giddings |
| 4,147,621 A | 4/1979 | Giddings |
| 4,214,981 A | 7/1980 | Giddings |
| 4,250,026 A | 2/1981 | Giddings et al. |
| 4,440,638 A | 4/1984 | Judy et al. |
| 5,039,426 A | 8/1991 | Giddings |
| 5,133,844 A | 7/1992 | Stevens |
| 5,156,039 A | 10/1992 | Giddings |
| 5,160,625 A | 11/1992 | Jonsson et al. |
| 5,454,945 A | 10/1995 | Spearman |
| 5,569,367 A * | 10/1996 | Betts et al. ............. 204/547 |
| 5,715,946 A * | 2/1998 | Reichenbach ........... 209/156 |
| 6,136,171 A | 10/2000 | Frazier et al. |
| 6,180,956 B1 | 1/2001 | Chondroudis et al. |
| 6,192,764 B1 | 2/2001 | Jiang et al. |
| 6,287,832 B1 | 9/2001 | Becker et al. |

(Continued)

FOREIGN PATENT DOCUMENTS

DE    19860118    9/2000

(Continued)

OTHER PUBLICATIONS

Giddings, "Field-Flow Fractionation: Analysis of Macromolecular Colloidal, and Particulate Materials," Science, vol. 260, pp. 1456-1465, (1993).

(Continued)

*Primary Examiner*—Nam X Nguyen
*Assistant Examiner*—Bach T Dinh
(74) *Attorney, Agent, or Firm*—Fay Sharpe LLP

(57) ABSTRACT

A flow cell is disclosed for collecting and concentrating a sample dispersed in a flowing medium. The collected sample can be selectively manipulated within the cell by the use of one or more traveling wave grids. The cells are particularly useful as bio-enrichment devices and can be utilized upstream of conventional analytical or detection instruments.

22 Claims, 13 Drawing Sheets

U.S. PATENT DOCUMENTS

| | | | |
|---|---|---|---|
| 6,296,752 B1 * | 10/2001 | McBride et al. ............. 204/547 |
| 6,355,491 B1 | 3/2002 | Zhou et al. |
| 6,692,627 B1 | 2/2004 | Russell et al. |
| 7,063,778 B2 * | 6/2006 | Mpholo et al. .............. 204/547 |
| 7,204,139 B2 * | 4/2007 | Takayama ................ 73/204.26 |
| 2001/0007775 A1 * | 7/2001 | Seul et al. ................... 436/534 |
| 2003/0077599 A1 * | 4/2003 | Sogard ........................... 435/6 |
| 2003/0159932 A1 | 8/2003 | Betts et al. |
| 2004/0000519 A1 | 1/2004 | Jiang et al. |
| 2005/0247564 A1 * | 11/2005 | Volkel et al. ................ 204/600 |

FOREIGN PATENT DOCUMENTS

| | | |
|---|---|---|
| WO | WO 97/27933 | 8/1997 |
| WO | WO2004008142 * | 1/2004 |

OTHER PUBLICATIONS

Lean et al., "High Speed MEMS Device for Sample Preparation of Bio-Agents in Water", $2^{nd}$ Joint Conference on Point Detection for Chemical and Biological Defense, pp. 1-21, (2004).

Auerswald et al., "Quantitative assessment of dielectrophoresis as a micro fluidic retention and separation technique . . . ", Microelectronic Engineering, Elsevier Publishers BV. vol. 67-68, pp. 879-886, (2003).

* cited by examiner

FLOW CONDUIT —110

PRE-FILTRATION
120

ULTRA-FILTRATION
130

AEROSOL COLLECTOR —160

BIO ENRICHMENT —140

DETECTOR —150

BIO-ENRICHMENT DEVICE TO ENHANCE SAMPLE COLLECTION AND DETECTION

STATEMENT REGARDING FEDERALLY SPONSORED RESEARCH OR DEVELOPMENT

This invention was made with Government support under W911NF-04-C-0034 awarded by the U.S. Army. The Government has certain rights in this invention.

BACKGROUND

The present exemplary embodiment relates to instruments or devices for collecting particles or samples, particularly from flowing streams. It finds particular application in conjunction with the detection of biological agents, and will be described with particular reference thereto. However, it is to be appreciated that the present exemplary embodiment is also amenable to other like applications.

Bio-agents dispersed either in aerosol form or in water are typically in such low concentrations that they are below the limit of detection (LOD) of even the most sensitive detection schemes. Yet, the ingestion of even a single bacterium may lead to fatal consequences. Accordingly, regardless of whether the sample is derived from aerosol or water collection, there exists a need to further concentrate the sample prior to detection.

Aerosol collection schemes typically sample large volumes of air at very high rates (up to 150 kL/min), and use either a cyclone or a virtual impactor design to collect particles having a size in the threat range and capture them in a wet sample of 5-10 mL volume. This hydrosol is then used as the test sample for agent detection. In order to use currently available detection strategies, it would be desirable to further concentrate the hydrosol by another two orders of magnitude. For example, this could be achieved by collecting all the bio-particles in the sample volume within a smaller volume of 50-100 µL.

Contaminants in water are typically treated by several filtration steps to recover the sample for agent testing. After initial pre-filtration to remove larger vegetative matter, the sample is further concentrated by two to three orders of magnitude using ultra-filtration. This method of tangential flow filtration (TFF) is laborious as it requires multiple sequential steps of TFF; each step utilizing a filter of lower molecular weight (MW) cut-off, and recycling of the retentate. The limiting factor for TFF is system loss, where there is a cut-off below which it may not provide any further improvement in concentration. The supernatant at the end is approximately a 50 mL volume to be presented to the detector. It would be particularly desirable to further concentrate the hydrosol by up to another three orders of magnitude.

Field Flow Fractionation (FFF) is a technique that allows the separation of particles of different charge to size ratios (q/d) in a flow channel. This technique is useful in many fields ranging from printing to biomedical and biochemical applications. Separation is achieved because particles with different q/d ratios require different times to move across the flow channel, and therefore travel different distances along the flow channel before arriving at a collection wall. To obtain well-defined and separated bands of species with different q/d values, the particles are typically injected through a narrow inlet from the top of the channel. Total throughput depends on the inlet geometry and flow rate, which in turn affects the q/d resolution of the system.

FFF relies upon the presence of a field perpendicular to the direction of separation to control the migration of particles injected into a flow field. The separated components are eluted one at a time out of the system based on retention times, and are collected in a sequential manner. The separations are performed in a low viscosity liquid, typically an aqueous buffer solution, which is pumped through the separation channel and develops a parabolic velocity profile typical of Poissieulle flow. The process depends on controlling the relative velocity of injected particles by adjusting their spacing from the side walls. Particles with higher electrophoretic mobility or zeta potential will pack closer to the walls and therefore move slower than those that are nearer the center of the channel. In effect, particles move at different rates through the system based on zeta potential and size. Use of different separation mechanisms such as thermal, magnetic, dielectrophoretic, centrifugation, sedimentation, steric, and orthogonal flow has given rise to a family of FFF methods. Although satisfactory in many respects, there remains a need for an improved FFF separation technique.

The present exemplary embodiment contemplates a new and improved bio-enrichment system, device, cells, and related methods which overcome the above-referenced problems and others.

BRIEF DESCRIPTION

In accordance with one aspect of the present exemplary embodiment, a device adapted for collecting particulates from a flowing medium is provided. The device comprises a body defining an inlet, an outlet, and opposing bottom and top walls extending at least partially therebetween and defining an expansion cavity. The cavity includes a collection wall extending from a downstream region of the bottom wall. The device also comprises a traveling wave grid disposed along the bottom wall and adapted to transport particulates proximate to the grid, to the collection wall.

In accordance with another aspect of the present exemplary embodiment, a bio-enrichment device is provided. The bio-enrichment device comprises a cell body defining an inlet, an outlet, an inlet wall, a collection wall opposite from the inlet wall, a bottom wall extending between the inlet wall and the collection wall, and a top wall extending between the inlet and the outlet and opposite from the bottom wall. The inlet wall, the collection wall, the bottom wall, and the top wall define an expansion cavity. The bio-enrichment device further comprises a first traveling wave grid disposed on the bottom wall. The bio-enrichment device also comprises a second traveling wave grid extending along the collection wall. The cell body further defines at least one sample collection port at a region proximate one of the first traveling wave grid and the second traveling wave grid. Upon operation of the device and admittance of a flowing medium containing bio-agents dispersed therein to the inlet defined in the body, bio-agents are collected at one or more of the sample collection ports.

In accordance with yet another aspect of the present exemplary embodiment, a method is provided for collecting and concentrating bio-agents from a flowing medium. The method comprises providing a hybrid flow cell including (i) a body defining an inlet, an outlet, opposing bottom and top walls extending at least partially therebetween and defining an expansion cavity, the cavity including a collection wall extending from a downstream region of the bottom wall, and (ii) a traveling wave grid disposed along the bottom wall and adapted to transport particulates proximate to the grid to a destination location. The method also comprises introducing the flowing medium containing bio-agents to the inlet of the flow cell. The method further comprises activating the traveling wave grid disposed on the bottom wall to thereby collect bio-agents from the flowing medium and transport the collected bio-agents to the destination location. The concentration of bio-agents as measured at the destination location is greater than the concentration of bio-agents as measured at the inlet.

BRIEF DESCRIPTION OF THE DRAWINGS

FIG. 1 is a schematic of an exemplary embodiment bio-enrichment system.

FIG. 2 is a schematic planar view of an exemplary embodiment field flow fractionation and traveling wave assembly hybrid bio-enrichment cell.

DETAILED DESCRIPTION

Figure 3:
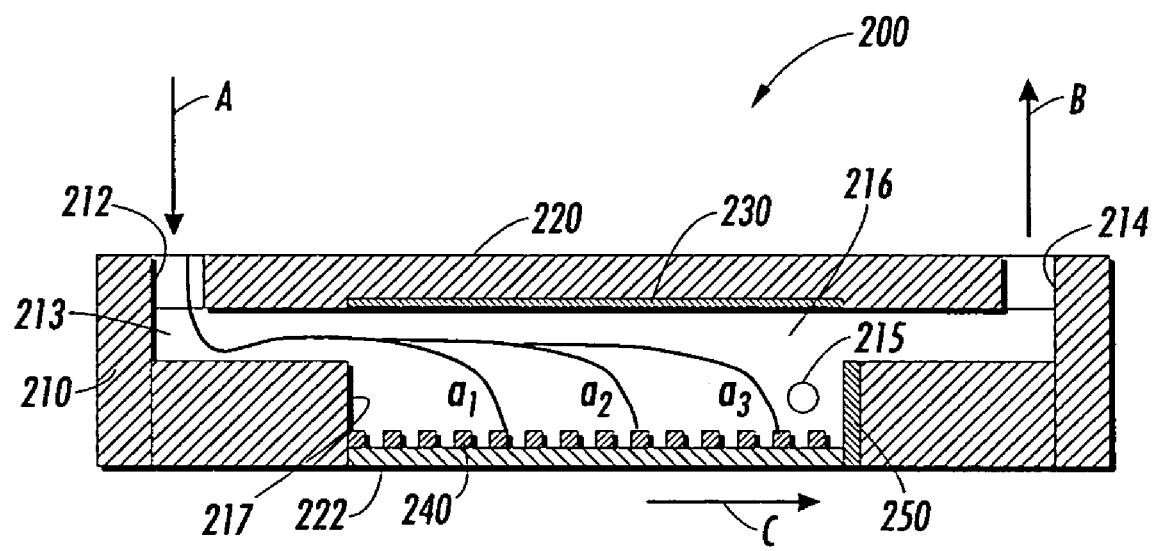
FIG. 3 is a schematic side elevational view of the cell taken along line 3-3 in FIG. 2.

The exemplary embodiment relates to bio-enrichment systems, devices, cells and methods that can perform initial separation (by charge/diameter, herein designated as q/d) of a sample mixture, followed by a concentration step. The exemplary embodiment can serve as either the back-end to collection strategies or the front-end to detection strategies. Specifically, the exemplary embodiment provides a system 100 as shown in FIG. 1 for sample concentration. FIG. 1 collectively depicts two separate systems, as follows. The system 100 concentrates a retentate by another two to three orders of magnitude. The system 100 comprises a flow conduit 110 through which a flow containing a sample to be detected travels. The flow is sampled and that portion is directed to a pre-filtration unit 120 which removes relatively large particles, contaminants, or other undesirables. The filtered sample is then directed to an ultra-filtration unit 130 which performs another filtering operation. The retentate from the ultra-filtration unit 130 is directed to an exemplary embodiment bio-enrichment cell 140 as described herein. The output of the cell 140 can then be directed to a conventional detector unit 150. Exemplary volume reductions and thus degrees of concentration for this sampling configuration are as follows. For a 50 L volume from unit 120 to 130, the retentate from unit 130 to the cell 140 is about 50 ml, and the supernatant volume from the cell 140 to the detector 150 is about 50 to 100 µl.

As previously noted, the exemplary embodiment also provides systems for concentrating an aerosol sample. This strategy is also depicted in FIG. 1 in which an aerosol collector 160 receives a sample from a suitable source. The output of the collector is then directed to the bio-enrichment cell 140, the output of which can then be directed to the detector 150 as previously explained. Exemplary volume reductions and thus degrees of concentration for this sampling configuration are as follows. For a 5 to 10 ml volume of hydrosol exiting the aerosol collector 160, the output of the bio-enrichment cell is about 50 to 100 µl.

The bio-enrichment device of the exemplary embodiment uses field flow fractionation (FFF) to initially deposit bio-matter onto a lower surface patterned with a planar inter-digitated traveling wave electrode grid as a function of q/d. The inter-digitated electrodes are driven in 4-phases (or n phases with n>2) with a traveling wave (TW) of voltage pulses to move the deposited bio-matter to an edge or region on the grid where another orthogonal TW array collapses the edge into a sample well. The resulting concentration is achieved by collecting bio-particles of the same q/d range within a much smaller volume of fluid. This technique will work for all material with a net charge or zeta potential. As a front-end to detection, the separation function increases selectivity, while the concentration function increases sensitivity. The concentrated sample may be transferred by micropipette for immunoassay. For compact and potentially autonomous operation, the bio-enrichment cell may be directly connected to a microfluidic channel into which analytes may be selectively metered, sorted, and transported with hydraulic and electro-osmotic flow (EOF) pumps through a series of orthogonal hybrid detectors for interrogation and agent identification.

The term "traveling wave grid" as used herein, collectively refers to a substrate, a plurality of electrodes to which a voltage waveform is applied to generate the traveling wave (s), and one or more busses, vias, and electrical contact pads to distribute the electrical signals (or voltage potentials) throughout the grid. The term also collectively refers to one or more sources of electrical power, which provides the multi-phase electrical signal for operating the grid. The traveling wave grids may be in nearly any form, such as for example a flat planar form, or a non-planar form. The non-planar form can be, for example, in the form of an arcuate region extending along the outer wall of a cylinder. The non-planar grid could be in the form of an annular grid defined within an interior region of a tube. Traveling wave grids, their use, and manufacture are generally described in U.S. Pat. Nos. 6,351, 623; 6,290,342; 6,272,296; 6,246,855; 6,219,515; 6,137,979; 6,134,412; 5,893,015; and 4,896,174, all of which are hereby incorporated by reference.

Figure 4:
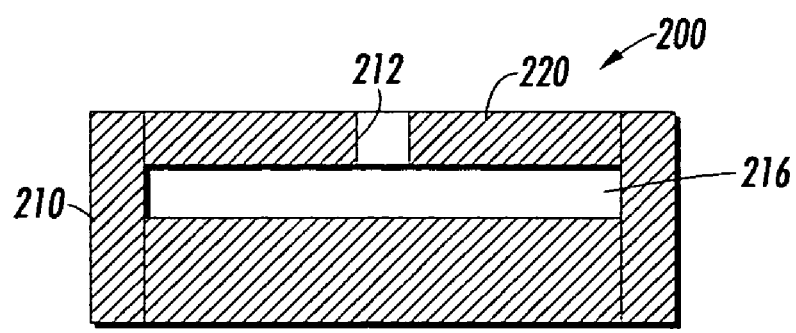
FIG. 4 is a schematic end view of the cell taken along line 4-4 in FIG. 2.
Figure 5:
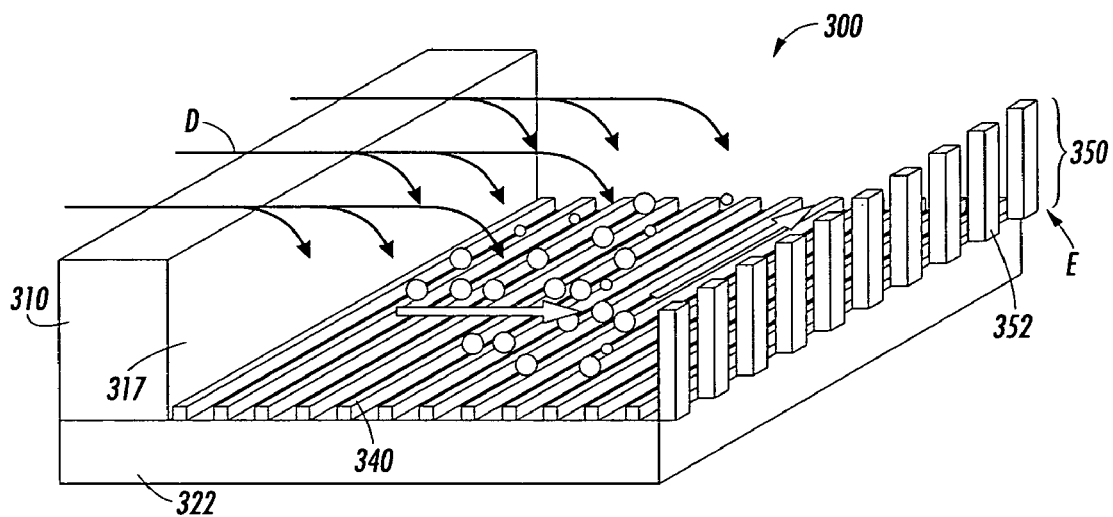
FIG. 5 is a perspective schematic illustration illustrating flow in another exemplary embodiment bio-enrichment cell.

The bio-enrichment cell uses both field flow fractionation (FFF) and traveling wave (TW) mechanisms. Various aspects of an exemplary embodiment bio-enrichment cell are shown in FIGS. 2-4 which cell includes thin inlet and outlet channels and a recessed expansion cavity. The roof of the cavity provides a continuous indium tin oxide (ITO) surface while the bottom provides a TW electrode array. A DC bias is maintained to provide an electric E field orthogonal to the direction of fluid flow. Purely laminar flow is required in the cavity for uniform separation. In FFF, bio-particles are deflected (as such occurs in a mass spectrometer) downwards due to their q/d or zeta potential, with the higher q/d particles depositing first or closest to the lead edge of the cavity. A 90 degree or angled bend at the inlet is utilized to defuse the flow to result in a more laminar flow field over the expansion cavity area where angled flow impingement would be undesirable. The expansion into the cavity slows down the flow to lower the requirement for bias deflection voltage and in turn a shorter TW dimension. It also allows more time for the bio-particles to respond to the applied electric field. The recessed cavity also acts to trap bio-particles, especially in the vortex or re-circulation area created at the bottom right corner of the flow cell thus keeping the bio-particles tightly focused. TW voltages are then used to move the deposited bio-particles as desired. In one embodiment, the TW moves bio-particles to a collection wall where an orthogonal TW grid as shown in FIG. 5 further re-directs the bio-particles to one corner, thus further concentrating them.

Specifically, referring to FIGS. 2-4, an exemplary embodiment bio-enrichment cell 200 is depicted. The cell 200 comprises a body 210 defining an inlet 212, an outlet 214, and an interior hollow region 216 generally extending therebetween. It is preferred that the inlet 216 include an angled region or bend, and ideally a 90 degree bend, such as bend 213. The cell body 210 also defines a sample discharge port 215. The interior hollow region 216 or expansion cavity is defined between an upper wall 220, and a lower wall 222. Disposed on the upper wall 220 and directed toward the interior region 216 is a planar electrode 230, which as previously noted, can be formed from a thin layer of ITO. A plurality of closely spaced TW electrodes forming a primary grid 240 are disposed on the lower wall 222. The cell 200 also comprises a collection wall 250 generally extending at right angles with respect to flow within the cell, and positioned along the downstream side of the TW grid 240. The wall 250 is in the form of a plurality of closely spaced TW electrodes 252. Defined at an opposite end of the region 216, from the collection wall 250, is an inlet wall 217.

Referring further to FIGS. 2-4, a flow stream containing sample to be collected enters the cell 200 through the inlet 212 as shown by arrow A. The stream enters the interior hollow region 216 or expansion cavity of the cell. The bend 213 within or proximate the inlet 212 serves to promote laminar flow once the flow stream enters the expansion region 216. Once the flow stream enters region 216, the velocity of the stream decreases. Concurrently, the TW grid 240 provides a bias deflection voltage or electric field that attracts or otherwise deflects the flow of sample in the flowstream. Exemplary flow lines $a_1$, $a_2$, and $a_3$ depict flow lines for three particles having different q/d ratios. Particles having relatively high q/d ratios will exhibit greater deflections, and so be displaced toward the grid 240 sooner. In contrast, particles having lower q/d ratios will be directed toward the grid 240 proximate the collection wall 250. The TW grid is operated to transport collected particles or sample in the direction of arrow C. Collected sample is transported along the wall 250 toward the sample discharge port 215. The exiting flow travels out of the cell 200 through the outlet 214 and as shown by arrow B.

The configuration of the exemplary embodiment cell 200 provides several significant advantages. Due to the flows through the cell, normal or perpendicular impingement of sample with the TW grid 240 is avoided. The cell 200 achieves generally laminar flow within its interior with negligible in-plane velocity on the TW grid 240. The recessed nature of the expansion region 216, with regard to the inlet 212, serves to reduce velocity of the sample and promote collection of the sample. In addition, the cell 200 enables incremental processing of a partial volume of a greater flow, such as that from which flow A originates.

Figure 6:
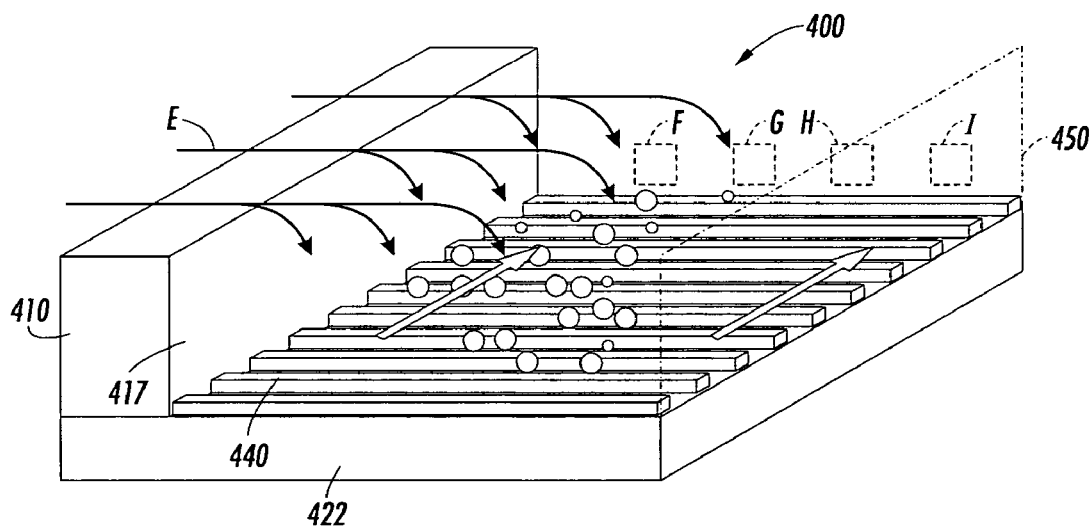
FIG. 6 is a perspective schematic view illustrating flow within another exemplary embodiment bio-enrichment cell.

The bio-particles distributed in the expansion region are sequentially pushed onto a surface, e.g. the collection wall, then collapsed into an edge and finally concentrated into a much smaller volume for sample collection. An estimate of the concentration factor as the particles-undergo these operations is the ratio of the initial volume to the final volume into which most of the bio-particles are collected. Typical initial volumes may be 5-50 mL so if the final volume is 50-100 mL, concentration factors of 100×-1000× are theoretically possible. The limit to the linear volume dimension is backdiffusion to counter electrodynamic drift. A simple estimate is given by E(w/2)=kT/q, where E, w, k, T, q are respectively, E field, width of the final sample volume, Boltzmann constant, temperature, and particle charge, respectively. By increasing the local E field by an order of magnitude, the band may be compacted by up to 10×. The diffusion length, R, over a time, t, is given by R2=(kT/phr)t, where h is viscosity and r is the particle radius. For bio-particles in the 1-10 μm range, the diffusion distance is only a few microns per second. Smaller protein-sized particles may experience more diffusion and therefore require continuous TW operation and the optimal selection of TW pitch to contain the diffusion. Alternatively, small bio-particles can be concentrated into a higher-viscosity medium, such as a gel, to reduce diffusion.

In another exemplary embodiment bio-enrichment cell 300, a TW grid moves bio-particles to a collector wall where another orthogonal TW grid as shown in FIG. 5 further re-directs the bio-particles to one corner, thus concentrating them. Operations can be sequenced so that after separation into bands, each band may be moved in turn against a lateral edge where it can either be concentrated into the sample well for detection, or purged by reversing the direction of the traveling wave. Therefore, only the particular band of interest (or q/d range of interest) is moved into the detection zone. Other uninteresting bands may be purged as desired.

Specifically, the cell 300 comprises a cell body 310, in which an expansion region is defined between an inlet wall 317, a collection wall 350 which is in the form of a TW grid 352, and a primary TW grid 340 extending along a lower wall 322. It will be understood that the body 310 includes an upper wall (not shown) having an appropriate inlet and outlet. An incoming flow stream D enters the expansion region at which particles in the stream are drawn toward the grid 340 and collected therein. The grid 340 is operated to transport the particles toward the second TW grid 350 which is preferably oriented transversely with respect to the grid 340 and disposed at a location furthest downstream within the expansion cavity. As particles collect on or near the second grid 350, that grid is operated to transport particles to a desired location along the grid 350, such as at location E at which the collected particles can be transported for subsequent detection or analysis. As previously explained with regard to the cell 200, in the cell 300, particles having a relatively high q/d ratio will deposit on the grid 340 closer to the wall 317.

Another exemplary embodiment bio-enrichment cell 400 is shown in FIG. 6 where separated bands may be concentrated in parallel against a side wall. The orientation of the TW grid is perpendicular to the previous embodiment depicted in FIG. 5, and should have little effect on separation since use of an electrode pitch of 40 mm is much less than a typical cell height of 1.5 mm. By adding another TW grid at the side wall where the different bands are concentrated, one can move each band sequentially into one corner where it can either be concentrated into the sample well for detection, or purged by reversing the direction of the traveling wave.

Specifically, the cell 400 includes a cell body 410 in which an expansion region is defined between an inlet wall 417, a collection wall 450, and a TW grid 440 extending along a lower wall 422. It will be understood that the body 410 includes an upper wall (not shown) having an appropriate inlet and outlet. An incoming flow stream E enters the expansion region at which particles in the stream are drawn toward the grid 440 and collected thereon. The electrodes of the grid extend parallel to the direction of flow of stream E in contrast to the configuration of the cell 300 in FIG. 5. Upon collection or deposition of particles on the grid 440 in the cell 400, the grid 440 is operated to transport bands of particles toward a desired location on or relative to the grid 440. Specifically, a collection of discrete locations or discharge ports can be defined along a side of the grid 440. A plurality of sample collection ports can be defined in one or more side walls of the cell body. Collected bands of particles on the grid 440 can be transported to one or more of the desired locations, while the particles are essentially maintained in their various separated populations. For example, a band of particles collected nearest the inlet wall 417, and so indicative of those particles having a relatively high q/d ratio, can be transported to location F by suitable operation of the grid 440. Conversely, a band of particles having a relatively low q/d ratio can be transported and collected at location 1. Similar bands of particles having q/d ratios within these populations having high and low q/d ratios, can be collected at locations G and H.

As will be appreciated, the TW grid extending along the collection wall is generally oriented at right angles to the TW grid disposed on the bottom wall of the cell body. However, the exemplary embodiment includes other configurations in which the TW grids are not transversely oriented. Additionally, the exemplary embodiment includes the use of a point electrode TW grid for either or both grids, and particularly as the TW grid disposed along the bottom wall. The use of a point electrode grid facilitates the passing of traveling waves in nearly any direction or path along the grid.

Figure 7:
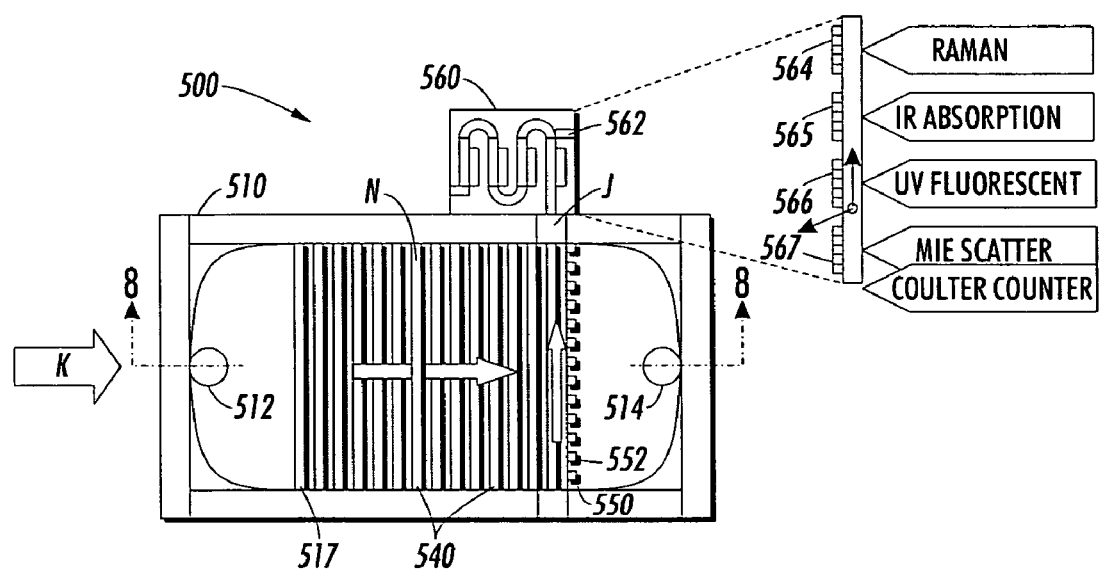
FIG. 7 is a schematic of another exemplary embodiment bio-enrichment cell.

The exemplary embodiment bio-enrichment devices provide excellent front-end processing to optical detection of bio-agents. Extension of sample concentrators to incorporate enrichment capabilities described herein provides a significant step towards allowing reagentless (for example specific binding, tagging, labeling, dyes or stains) identification of bio-agents. The exemplary embodiment bio-enrichment cell performs sample separation into bands according to q/d to increase selectivity, and can further concentrate the bands into sample wells to increase sensitivity. Interfacing of the sample wells with microfluidic channels further allows sequential interrogation of the sample analyte by a hybrid collection of detection schemes. FIG. 7 shows an exemplary embodiment cell incorporating a singular micro-fluidic channel connecting a sequential series of detection schemes which may comprise separate capabilities including: Coulter counter or MIE scattering; spectra from intrinsic UV fluorescent sources of possibly several excitation wavelengths (e.g. 280 nm and 350 nm); UV, visible and Far-IR absorption; and Raman spectroscopy.

Figure 8:
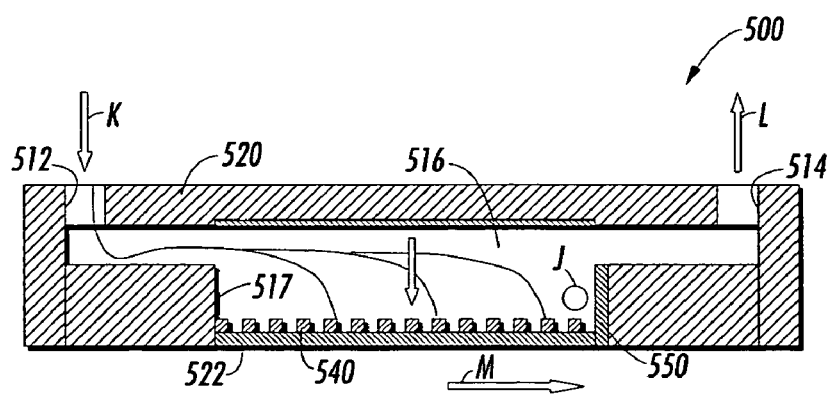
FIG. 8 is a schematic side view taken along line 8-8 in FIG. 7 illustrating flow through the cell.

Specifically, FIGS. 7 and 8 depict another exemplary embodiment bio-enrichment cell 500 comprising a cell body 510 having an inlet 512 for receiving a flow stream K, an outlet 514, an interior hollow expansion region 516 which generally extends between an upper wall 520, a lower wall 522, an inlet wall 517 and an oppositely disposed collection wall 550. A primary TW grid 540 is disposed on the lower wall 522 and a secondary TW grid 552 extends along the collection wall 550. A sample discharge port J is defined along a lateral location relative to the grids. As will be appreciated, upon operation of the cell, particles or sample are collected on the grid 540 and transported in the direction of arrow M toward the secondary grid 552. An exiting flow stream L passes through the outlet 514. Disposed proximate the discharge port J is a detector 560. The detector 560 is adapted to detect or otherwise analyze particles or sample collected and transported to the port J. Although a wide array of detectors 560 can be utilized, generally, the employed detector will include a purge 562 and utilize one or more detector arrays 564, 565, 566, and 567. The arrays can use any appropriate technology, however, it is contemplated to use Raman, IT absorption, UV fluorescence, MIE Scattering, Coulter Counters, and/or combinations of these techniques. It is often preferred, in certain applications to utilize a microfluidic channel having a serpentine configuration with multiple detector arrays constituting the detection unit 560.

The exemplary embodiment bio-enrichment cell as shown in FIGS. 7 and 8 can be operated to collect a specific separated band of sample or particles, transport that band to a particle collection port, thereby greatly increase the concentration of the collected sample or band, and then perform one or more analytical operations upon the collected band. In FIG. 7, a band of particles disposed on grid 540 denoted as band N is transported to the secondary TW grid 550. As will be appreciated, the band N may for example represent particles having a narrow range of q/d ratios. Upon transport to the grid 550, the particles formerly constituting band N are transported to port J at which they are introduced into the multi-array detector 560.

Figure 9:
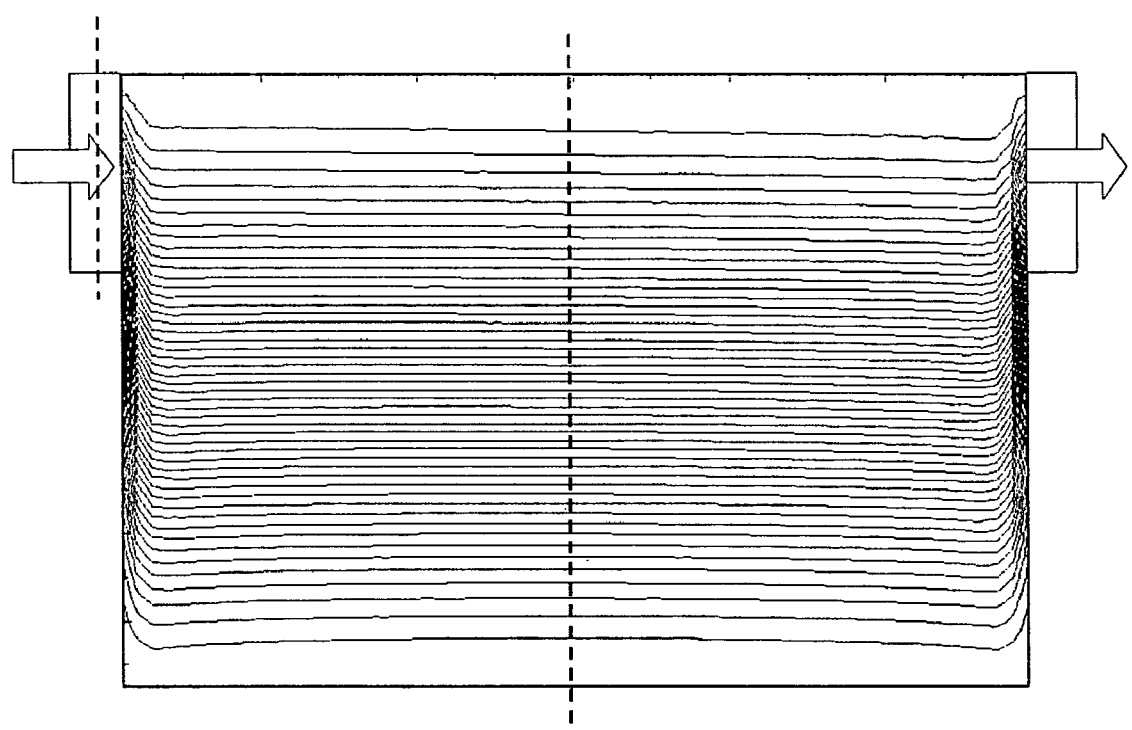
FIG. 9 illustrates laminar flow through the cell of FIGS. 7 and 8.
Figure 10:
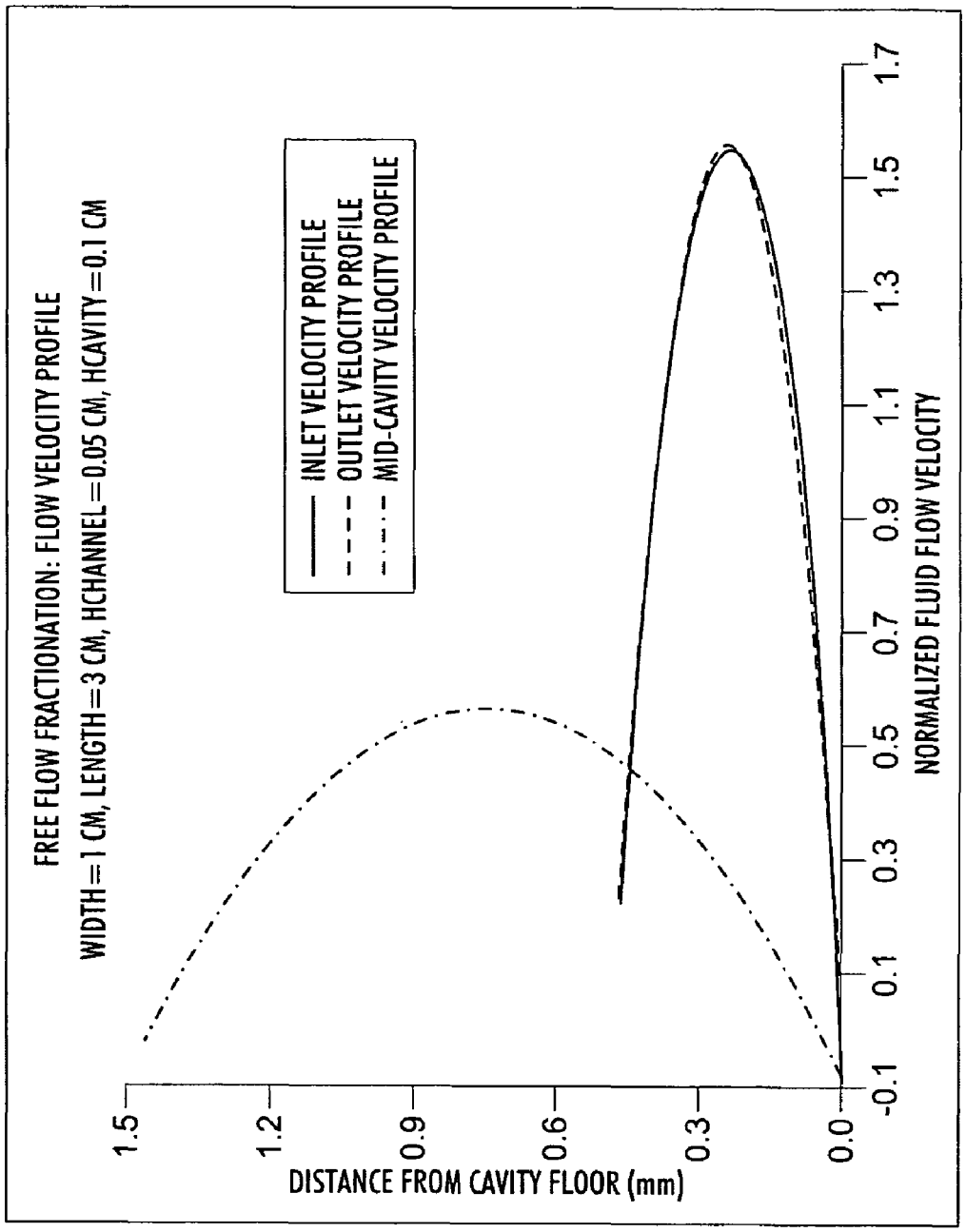
FIG. 10 is a graph illustrating free flow fractionation and flow velocity profiles in a typical exemplary embodiment cell.

A hybrid flow cell of 4.5 mL capacity, designed to handle sample volumes up to a liter, was fabricated using a vertically stacked configuration. Due to the low concentration involved and the slow flow regime, the Navier-Stoke's equation may be simplified to a more tractable viscous Stoke's model for the fluidics with velocity profiles dictated by Poisseuille flow. Bio-particle trajectories subjected to both hydrodynamic and electric forces were predicted. Gravity may be sufficient to maintain the slow velocities, rendering a pump unnecessary. FIG. 9 shows laminar flow streamlines and FIG. 10 shows Poisseuille velocity profiles at the inlet and mid-channel locations of such a flow cell.

Table 1 set forth below, shows various parameters assuming a 1 liter sample volume and a handling capacity of 4.5 mL. Clearly parameters may be optimized based on initial specification for sample volume and process time. Inter-dependent parameters, such as for example voltage, range of bio matter q/d or zeta potential, and cell dimension are selected to meet desired specifications. Total process time is the summation of flow separation (tFFF), and concentration (tTW), given by:

$$t_{FFF} = h^2/\mu V_{FFF}$$

$$t_{TW} = Ls/\alpha\mu V_{TW}$$

where u is the electrophoretic mobility, h is the FFF cell height, L is the FFF cell length, s is the spacing between TW traces, $V_{FFF}$ is the separation voltage, TW is the TW voltage, and a (~0.25) is a coefficient to represent the effective tangential E field within a spacing thickness above the plane of the TW traces.

embodiment bio-enrichment cells are integrable with one or more collection steps to attain about 100×-1000× increases in sensitivity. The exemplary embodiment bio-enrichment cells are integrable with detection steps to prepare samples with increased selectivity and about 100×-1000× increases in sensitivity. The exemplary embodiment bio-enrichment cells

TABLE 1

| $t_{Process}$ | Flow Rate <mL/s> | $V_x$ <cm/s> Channel | $V_x$ <cm/s> Cavity | q/d = 3 pC/cm $V_x/Y_y$ | Δx <cm> | qd = 6 pC/cm $V_x/Y_y$ | Δx <cm> | q/d = 9 pC/cm $V_x/Y_y$ | Δx <cm> |
|---|---|---|---|---|---|---|---|---|---|
| 10 | 1.6667 | 3.3333 | 1.1111 | 52.360 | 7.854 | 26.180 | 3.927 | 17.453 | 2.618 |
| 15 | 1.1111 | 2.2222 | 0.7407 | 34.906 | 5.236 | 17.453 | 2.618 | 11.636 | 1.745 |
| 20 | 0.8333 | 1.6667 | 0.5555 | 26.180 | 3.927 | 13.090 | 1.964 | 8.727 | 1.309 |
| 25 | 0.6667 | 1.3333 | 0.4444 | 20.944 | 3.142 | 10.472 | 1.571 | 6.981 | 1.047 |
| 30 | 0.5555 | 1.1111 | 0.3704 | 17.453 | 2.618 | 8.727 | 1.309 | 5.818 | 0.873 |
| 35 | 0.4762 | 0.9524 | 0.3175 | 14.960 | 2.244 | 7.480 | 1.122 | 4.987 | 0.748 |
| 40 | 0.4167 | 0.8333 | 0.2778 | 13.090 | 1.964 | 6.543 | 0.982 | 4.363 | 0.655 |
| 45 | 0.3703 | 0.7407 | 0.2470 | 11.635 | 1.745 | 5.818 | 0.873 | 3.879 | 0.582 |
| 50 | 0.3333 | 0.6667 | 0.2222 | 10.472 | 1.571 | 5.236 | 0.785 | 3.491 | 0.524 |
| 55 | 0.3030 | 0.6060 | 0.2020 | 9.520 | 1.428 | 4.760 | 0.714 | 3.173 | 0.476 |
| 60 | 0.2778 | 0.5556 | 0.1852 | 8.727 | 1.309 | 4.363 | 0.654 | 2.909 | 0.436 |

| $h_{chan}$ <çm> | L <cm> | W <cm> | $h_{eav}$ <cm> | A <$cm^2$> | $V_{chan}$ <mL> | η <kg/m · s> | ΔV <V> | $E_{yu}$ <V/cm> | g/d <ƒC/cm> | $v_y$ <cm/s> | $t_y$ <s> |
|---|---|---|---|---|---|---|---|---|---|---|---|
| 5.e−2 | 10.0 | 10.0 | 0.1 | 0.5 | 5.0 | 1.e−3 | 10 | 66.67 | 3 | 2.122e−2 | 7.069 |
| | | | | | | | | | 6 | 4.244e−2 | 3.543 |
| | | | | | | | | | 9 | 6.366e−2 | 2.356 |

A design for an integrated 3-layer TW module was fabricated and proof of concept was demonstrated by moving *Bacillus thurengiensis* in tap water. An electro-hydrodynamic particle model has been developed to simulate and predict the performance of the device.

The various exemplary embodiment bio-enrichment devices can perform initial separation (by charge/diameter, i.e. q/d) of a sample mixture, followed by a concentration operation. These various devices can serve as either the back-end to collection schemes or the front-end to detection strategies. These devices fill the niche for sample concentration currently addressed by ultra-filtration, and extends it by further concentrating the retentate by about another 100×-1000×.

The various exemplary embodiment bio-enrichment cells utilize a combination of hydrodynamic and electric forces to both separate and concentrate bio-agents (or any charged particles) from a fluid into a small volume element in continuous flow. In certain exemplary embodiments, a TW grid moves bio-particles to a collection wall where another orthogonal TW grid as shown in FIGS. 2, 3, 5, and 7 further re-directs the bio-particles to one corner, thus concentrating them. Operations can be sequenced so that after separation into bands, each band may be moved in turn against the collection wall where it can either be concentrated into a sample well for detection, or purged by reversing the direction of the traveling wave. Therefore, only the particular band of interest (or q/d range of interest) is moved into the detection zone. Other uninteresting bands may be purged as desired. As noted, the exemplary embodiment cells can be used as a bio-enrichment device as a front-end to detection by integrating a micro-fluidic interface to transport samples in a controlled manner as illustrated in FIG. 5.

The exemplary embodiment bio-enrichment cells exhibit numerous benefits, features, and advantages. The cells employ step-wise separation and concentration which allows increased flexibility in sample preparation. The exemplary feature no mechanical moving parts, low voltage and power operation, are highly portable, and are easily optimized for prescribed sample volume and process time. The exemplary embodiment devices or cells can be in the form of a compact, low power, port-able device for bio-enrichment. The exemplary embodiment devices or cells provide increased selectivity by initial separation into bands according to q/d range and increased sensitivity with subsequent concentration of the previously separated bands. The devices or cells may be integrated as front-end to detection systems for 100×-1000× increase in sensitivity. The devices or cells may be integrated as back-end to collection systems for 100×-1000× increase in sensitivity. The devices or cells may be operated without flow to concentrate (without separation) a sample volume equal to the cavity size. The devices or cells may be dimensioned for various ranges of sample volume, and extended to re-circulating operation to ensure all biological matter is deposited onto the lower collection plate. Continuous TW operation sets up a compression force against the collection wall of the sample well to prevent back-diffusion of the concentrate and hence prevent band broadening.

The various exemplary embodiments also provide new configurations and layout of the FFF/TW cell to enhance flexibility of the design and enable parallel transfer of bands of bio-particles for subsequent bio-agent detection and identification. In this regard, the exemplary embodiment additionally modifies the traditional use of FFF to (i) allow deposition of separated bands on a side wall; (ii) introduces an expansion chamber to reduce the ratio of fluid to drift velocities so that larger sample volumes may be handled; and (iii) utilizes the use of a fin structure inside the expanding fractionation chamber, together with an electrode at the lower lip of the inlet, for field tailoring to enable higher resolution separation and deposition of narrower bands of similar q/d material. Electrostatic deflection pushes particulates to the upper flow region away from the lower region with most diverging streamlines. The trailing edge of the fin is also designed to allow fully developed parabolic flow with minimal divergence at the trailing edge. The following exemplary embodiment devices exemplify feature (iii).

The exemplary embodiment provides a unique variant strategy for FFF systems by incorporating several modifications to the geometry of a flow cell. Instead of eluting samples as in traditional FFF, the samples are deposited in the vicinity of a side wall within the channel for further processing. The objective is to separate particulates by q/d and deposit them into narrow bands in a distribution along the length of the channel wall. Analogous to mass spectrometry, particulates with higher q/d have shorter time-of-flight and deposit earlier or closer to the inlet. Narrower bands would allow easier discrimination in Δq/d and therefore correspond to increased resolution for detection or particulate identification. Deposited particulates on conducting substrates can be used for detection methods such as surface enhanced Raman scattering (SERS). Particulates in the vicinity of the wall where fluid velocity is minimal may also be further transported by other techniques and strategies. A further innovation is the creation of an expansion chamber to handle larger sample volumes and to reduce the ratio of convective flow to electrophoretic flow velocities, thus allowing also for lower voltage use. Typical FFF geometries are straight channels. This expansion introduces divergence of the flow streamlines at the inlet leading to increased concentration dispersion. A fin structure is introduced to reduce this initial particle dispersion by field tailoring of both electrostatic and flow components.

In a straight channel, the flow field and the electric field are always perpendicular to each other, or generally so, leading to orthogonal electrophoretic and drift velocities for the particle. In electroosmotic flow both of these velocities are constant and each particle is traveling in a straight line until it hits the side wall. In more complicated flows such as pressure driven flow, the particle trajectories will be more complicated. In order to achieve separation, particles of different charge to diameter ratio, q/d, released in a certain elevation Δy inside the channel have to make contact with the side wall at a lateral distance Δx. For any system where the fluid flow is always perpendicular to the electric field and the cross-section of the channel does not change, the separability (i.e. the ability to separate two species of different q/d) is independent of the applied field and flow rate, and depends only on the relative height $y_0/H$ where the particles enter the channel. However, analytic calculations show that in pressure driven flow separability can be better than for plug flow, if the particles are released close to the top wall of the channel.

Figure 11:
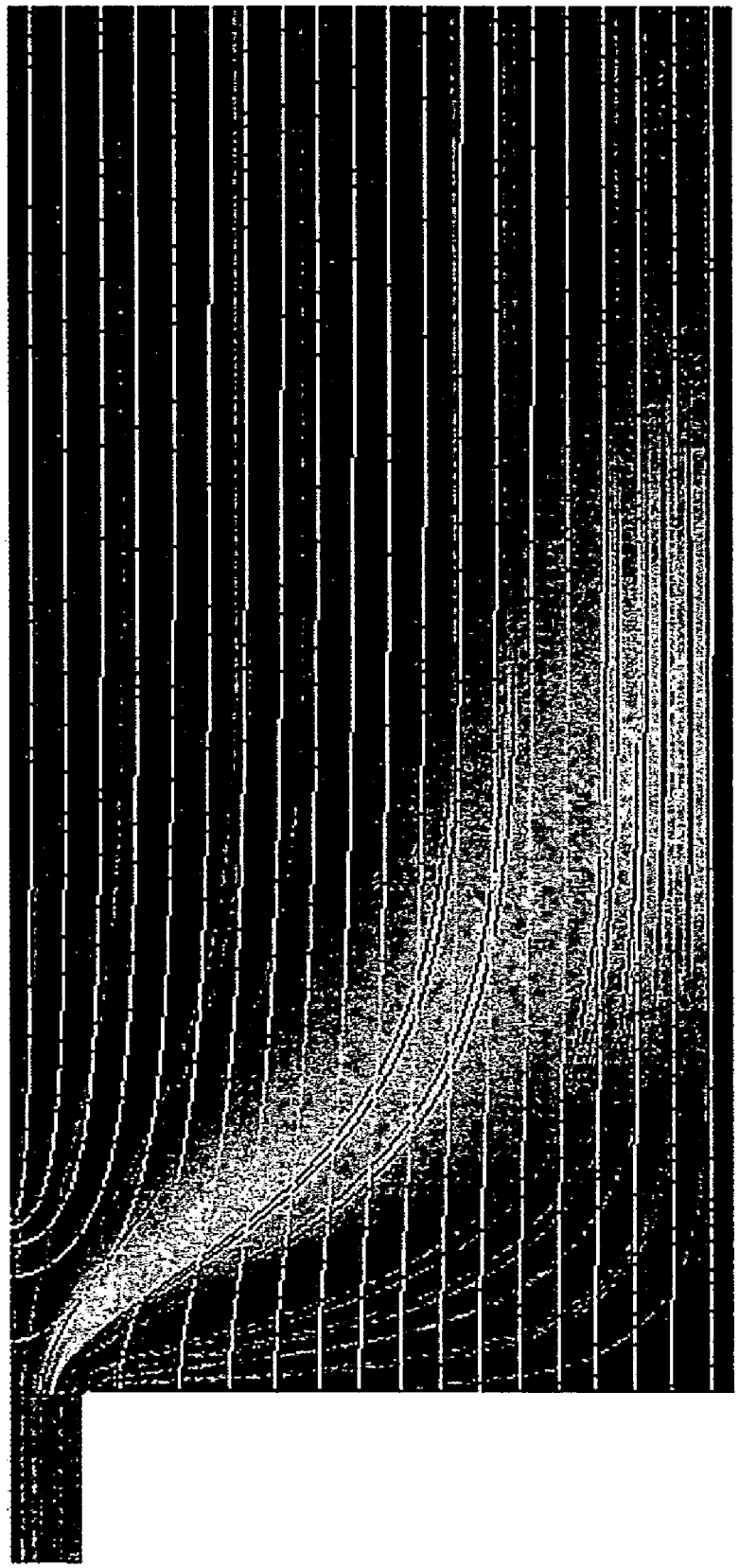
FIG. 11 is a side view illustrating typical flow lines through a simulated exemplary embodiment cell.

A simulation was performed using an exemplary embodiment cell. The inlet was 100 μm high and the FFF cell was 1 mm high and 2 to 4 mm long. The applied bias voltage was 1V, which ensured that particles with q/d<1 pC/cm would reach the cell bottom within the length of channel. At an inlet flow speed of 1 mm/s the flow was laminar and the stream lines expanded immediately into the flow cell. A small vortex formed at the inlet bottom corner of the FFF cell, which increased in size with increasing fluid velocity at the inlet. Microscopic particles that move along the streamlines followed this expansion, and, after being exposed to an electric field, deposited into rather broad bands on the channel floor, as shown in FIG. 11 by the highlighted cone extending downward from the cell inlet.

From the results derived for FFF in straight channels, narrow bands can be achieved. If the particles are injected close to the top wall of the cell very narrow bands can be achieved. Though the particles are initially close to the top wall in the flow cell shown in FIG. 11, this advantage is lost because the micron-sized particles of interest closely follow the stream lines. The ideal scenario is a case where the particles stay close to the top wall until after a parabolic flow profile is established in the flow cell, and before exposing the particles to the fractionation field.

Figure 16:
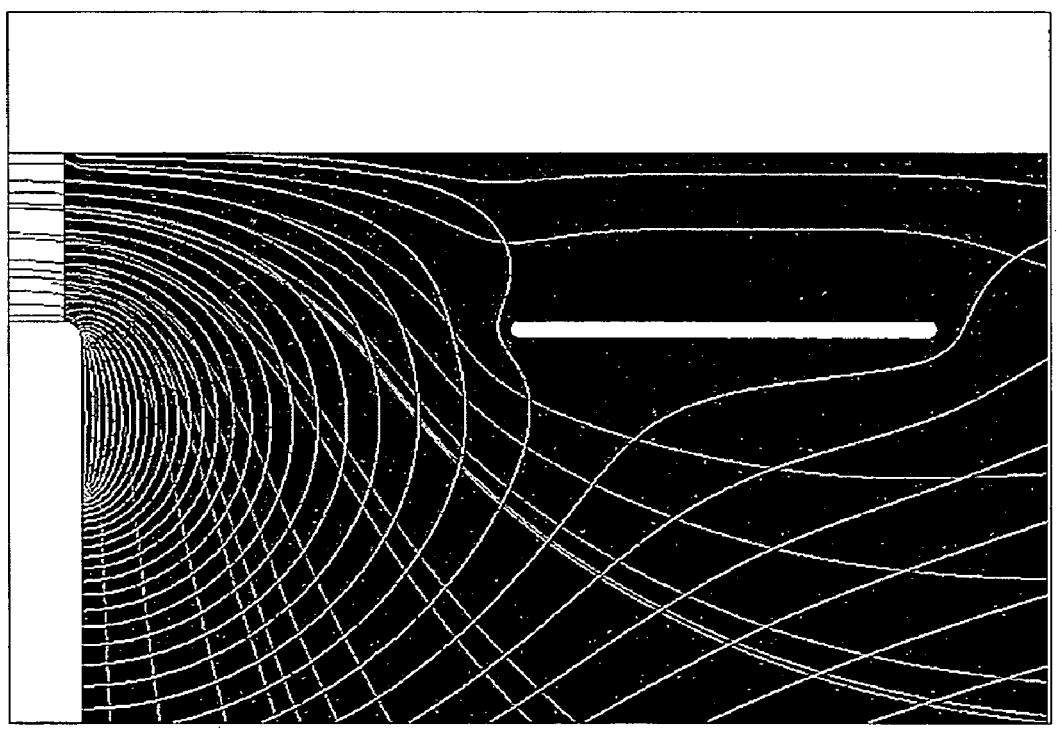
FIG. 16 is a side view illustrating flow lines through yet another exemplary embodiment flow cell.
Figure 17:
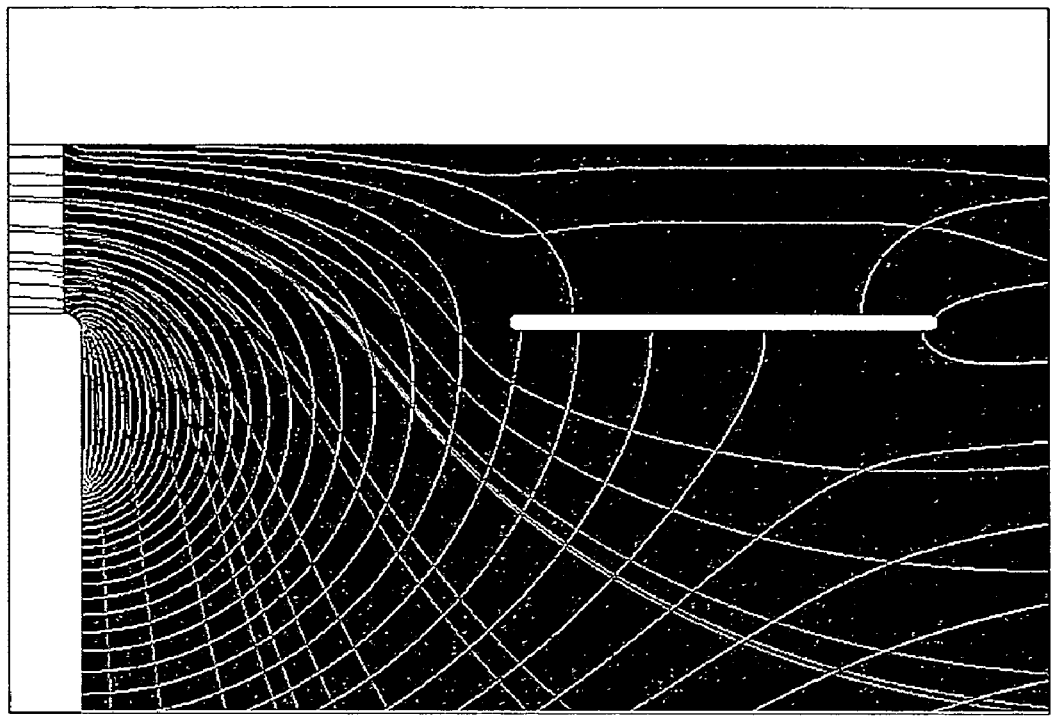
FIG. 17 is a side view illustrating flow lines through another exemplary embodiment flow cell.
Figure 18:
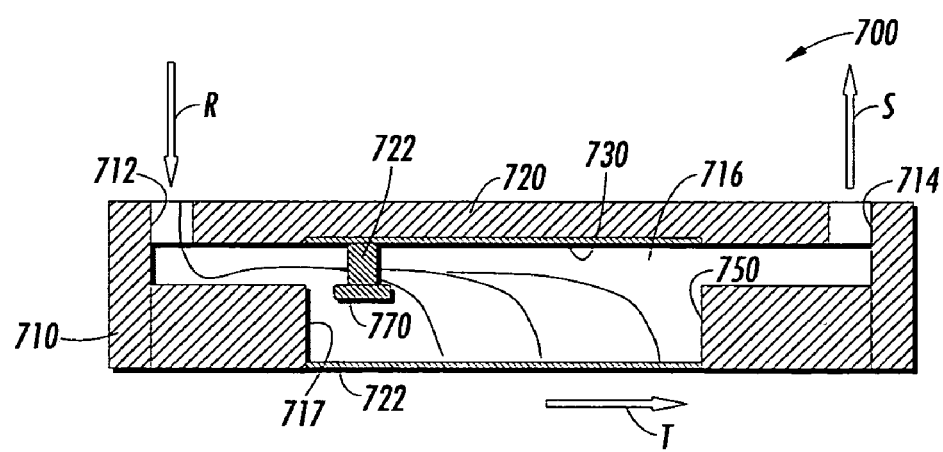
FIG. 18 is a side elevational schematic view of another exemplary embodiment flow cell depicted in FIG. 20, illustrating flow through the cell.
Figure 19:
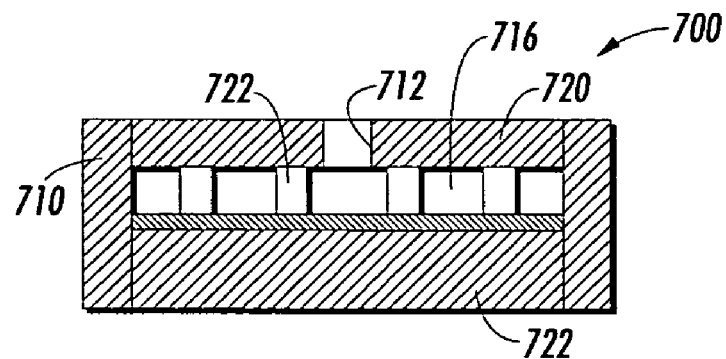
FIG. 19 is an end view illustrating the flow cell depicted in FIG. 20.
Figure 20:
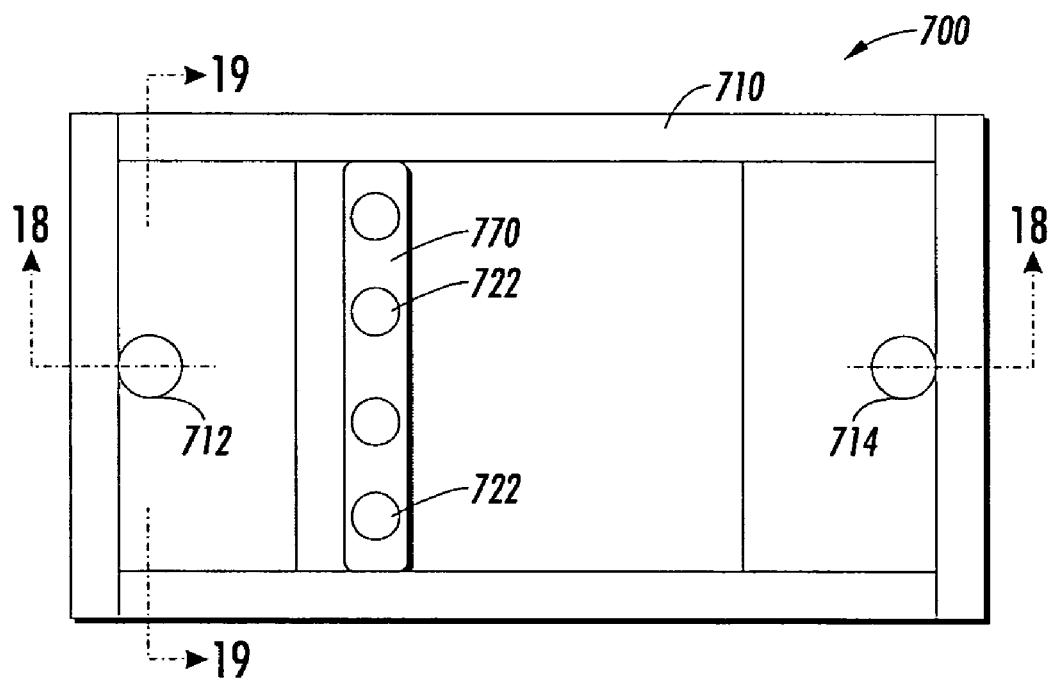
FIG. 20 is a top planar view depicting the exemplary embodiment flow cell shown in FIGS. 18 and 19.

FIGS. 12-15 illustrate another exemplary embodiment cell featuring the use of a fin structure to modify flow. A thin fin structure is placed in the FFF cell a short distance beyond the point of flow expansion. The incoming liquid still expands into the lower part of the cell, as shown in FIGS. 16 and 17, and at the trailing edge of the fin a nearly perfect parabolic profile is established inside the cell. The fin structure may be supported at the side walls of the chamber if the dimensions permit a more rigid assembly. The fins may also be attached to the top lid much like a "spoiler" with a finite number of SU-8 support posts, as shown in FIGS. 18-20.

Figure 12:
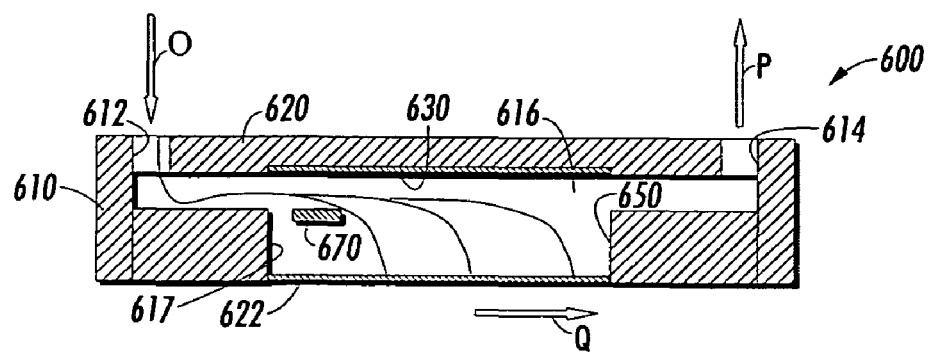
FIG. 12 is a cross-sectional schematic side view of another exemplary embodiment cell illustrating flow therethrough.
Figure 13:
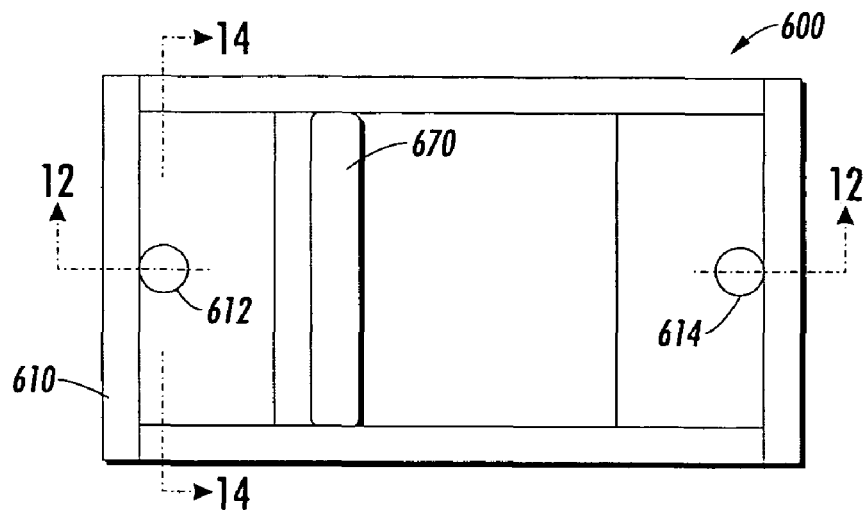
FIG. 13 is a top planar schematic view of the flow cell depicted in FIG. 12.
Figure 14:
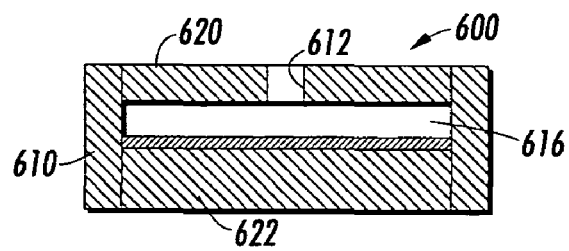
FIG. 14 is an end view of the flow cell of FIGS. 12 and 13.
Figure 15:
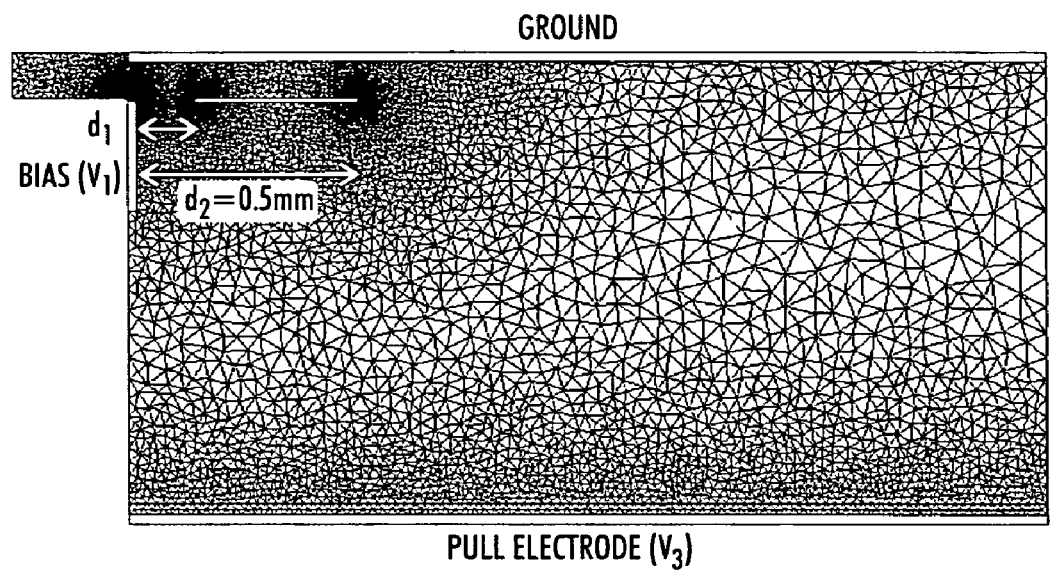
FIG. 15 is a side schematic view of another exemplary embodiment flow cell illustrating the use of a bias field.

Specifically, FIGS. 12-14 illustrate another exemplary embodiment bio-enrichment cell 600 comprising a cell body 610 defining an inlet 612, an outlet 614, an upper wall 620 and a lower wall 622. An expansion region 616 is defined therebetween. A planar electrode 630 is disposed along the underside of the upper wall 620. A primary TW grid (not shown) can be disposed along the upper surface of the lower wall 622. As will be appreciated from previous descriptions of alternate exemplary embodiment cells, sample or particles dispersed in an incoming flow stream O can be collected on the lower wall 622 and transported to a collection wall 650 which is generally opposite from an inlet wall 617. The particles are transported in the direction of arrow Q. The exiting flow leaves the cell as shown by arrow P. The cell 600 features a fin member 670 that serves to promote flow streams to extend in a direction parallel with the upper wall 620 for a sufficient distance or time, until after a parabolic flow profile is established in the cell 600, and prior to exposing the sample or particles to the fractionation field occurring in the region of expansion 616.

In order to keep the incoming particles or sample above the fin, a small force can be applied that urges them away from the streamlines that connect to the lower part of the fin. One strategy for achieving this is to apply a small bias field between the inlet wall of the FFF cell and the top wall ($V_1$ in FIG. 15). In this particular example, the top wall is grounded, the bias voltage at the inlet wall $V_1$ is positive in the event it is desired to fractionate particles with a positive q/d value, and the bottom wall has a negative voltage $V_3$. It has been discovered that a grounded fin yields best performance. This seems to be due to the fact that with a grounded fin there is no variation of the electric field in the volume between the fin and the top wall (see FIGS. 16 and 17), allowing the particles to follow the fluid unencumbered. FIG. 16 illustrates the electrical potential around a grounded fin. And, FIG. 17 illustrates electric potential around an insulated fin.

Note that for higher bias voltages the particles are pushed towards the top wall and a good anti-adhesion control is necessary to prevent particles from being retained there. If the bias voltage is too low, some or all particles will move below the fin and deposit in a broad peak at the bottom wall.

FIGS. 18-20 depict another exemplary embodiment bio-enrichment cell 700. The cell 700 comprises a cell boy 710 defining an inlet 712, an outlet 714, an upper wall 720 and a lower wall 722. An expansion region 716 is defined therebetween. A planar electrode 730 is disposed along the underside of the upper wall 720. A primary TW grid (not shown) can be disposed along the upper surface of the lower wall 722. As will be appreciated from previous descriptions of alternate exemplary embodiment cells, sample or particles dispersed in an incoming flow stream R can be collected on the lower wall 722 and transported to a collection wall 750 which is generally opposite from an inlet wall 717. Transport occurs in the direction of arrow T. Exiting flow leaves the cell as flow S. The cell 700 features a fin member 770 that serves to promote flow streams to extend in a direction parallel with the upper wall 720 for a sufficient distance or time, until after a parabolic flow profile is established in the cell 700, and prior to exposing the sample or particles to the fractionation field occurring in the region of expansion 716. The fin member 770 can be secured to the upper wall 720 by one or more posts 722.

Figure 21:
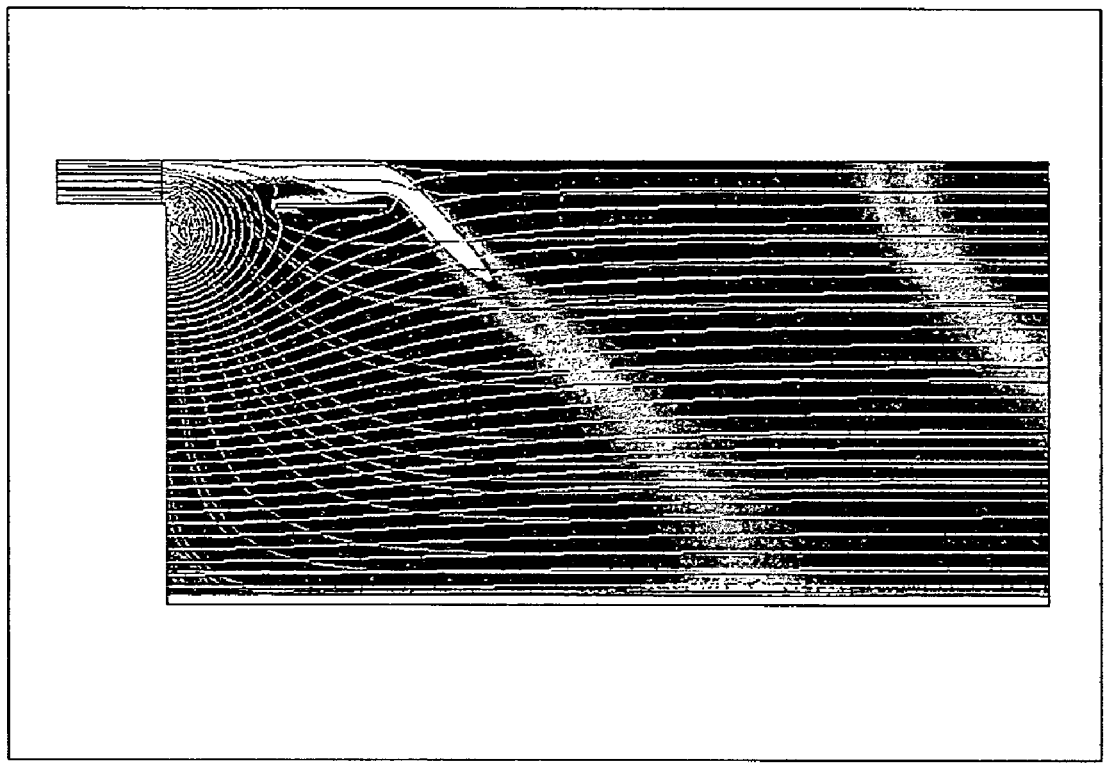
FIG. 21 is a side view illustrating flow lines through another exemplary embodiment flow cell.
Figure 22:
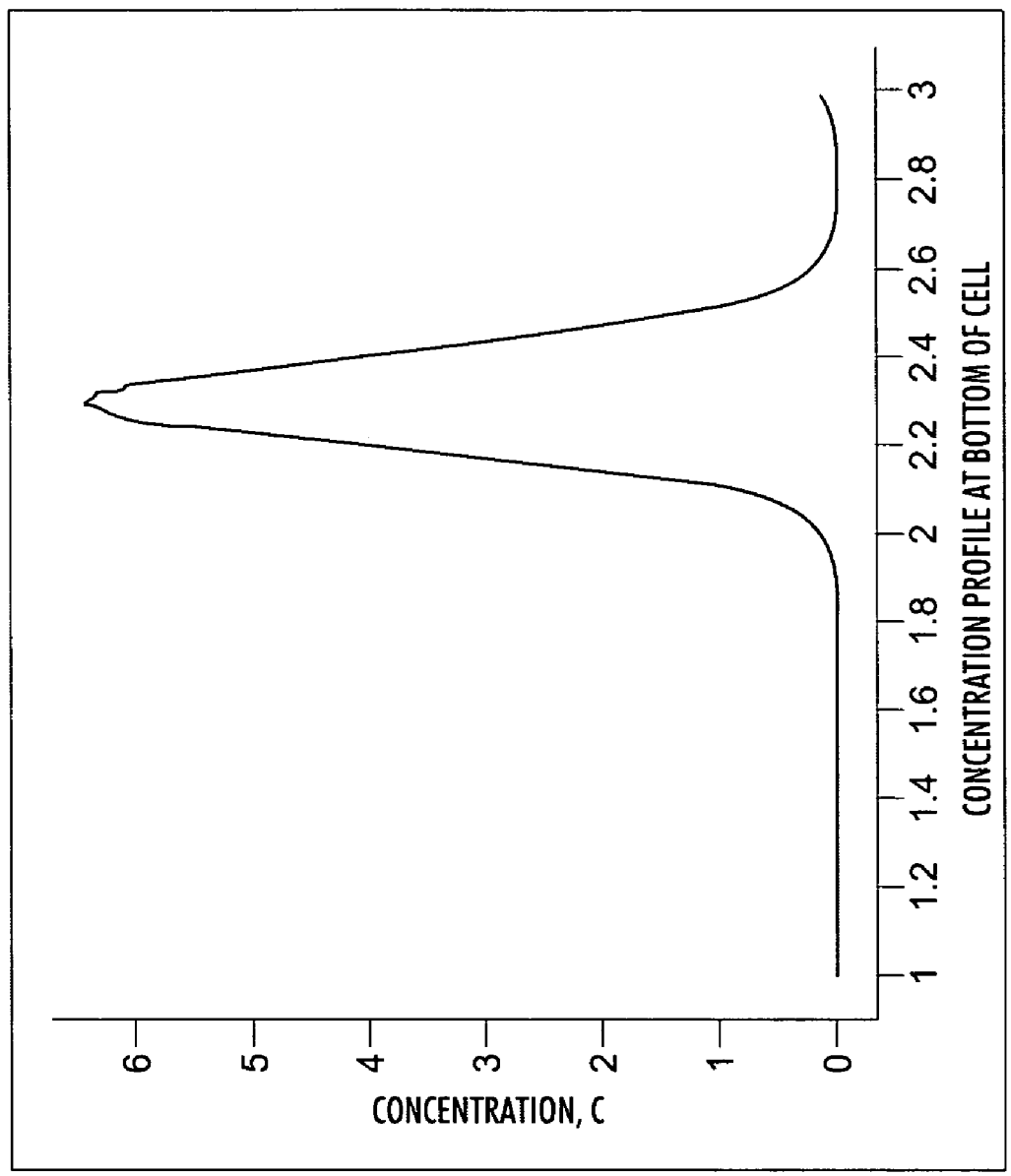
FIG. 22 is a graph illustrating the concentration profile at the bottom of a cell, the flow in which is depicted in FIG. 21.

For a maximum inlet velocity of 1 mm/s and particles in the q/d range about 1.6 pC/cm, a bias voltage of $V_1=0.5V$ is optimal, as can be seen from FIGS. 21 and 22. The particles stay close to the top wall until after they pass the fin. Once they are within reach of the bias field, they start moving towards the bottom wall and deposit in a well-defined and narrow peak (see FIG. 22).

These modified FFF geometries may be used for in-channel separation and deposition with narrow q/d bands in a closed system using an expansion channel. The use of an expansion chamber allows higher volume handling capacity within a shorter channel length without compromising throughput. Fin structure minimizes diverging flow dispersion. The separated q/d bands are narrower with the use of the fin structure, giving higher separation resolution. The deposited particulates may be in a form ready for SERS detection. Alternatively, the particulates are moved to a region of slow fluid flow where other forces may be used for further sample manipulation. Fin structure serves at least two purposes: (1) minimizes diverging flow dispersion; and (2) in combination with bias field such as V1 in FIG. 15, deflects particles to the top flow region away from the area of most diverging flow and recombines them with the fully developed flow profile for FFF.

The shape of the fin can be further optimized to facilitate fabrication. For example, existing streamlines form conforming shapes that approximate cross-sections that may be suitable fin geometries. So larger cross-section shapes may be considered which do not significantly alter the desired fully developed parabolic profile near the trailing edge.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A device adapted for collecting particulates from a flowing medium, the device comprising:
   a body defining an inlet including an inlet wall having an angled bend configured to diffuse a laminar flow medium, an outlet, opposing bottom and top walls extending at least partially therebetween and defining an expansion cavity, the expansion cavity including a collection wall, disposed orthogonally to the outlet, extending from a downstream region of the bottom wall, an upper surface of the inlet wall being in a plane distinct from an upper surface of the bottom wall, the expansion cavity contains a first path adjacent to the inlet and a second path adjacent to the outlet, each with a first height, and the expansion cavity with a height larger than the first height to connect the inlet and the outlet via the first path and the second path;
   a first traveling wave grid disposed along the bottom wall and adapted to transport particulates within a given charge to size ratio proximate to the grid, to the collection wall;
   a second traveling wave grid adjacent the collection wall and adapted to transport particulates to a destination location on the second traveling wave grid, wherein the second traveling wave grid transports particulates in a direction different from the direction particulates are transported by the first traveling wave grid; and
   a fin extending within the expansion chamber positioned such that the initial dispersion of the particulates is compacted by forcing a majority of the particulates to travel over the fin upon entering the expansion cavity, where the fin is generally elongated along a direction of the laminar flow.

2. The device of claim 1 wherein the concentration of particulates at the destination location is within the range of 100 to 1000 times the concentration of the particulates in the flowing medium at the inlet of the body.

3. The device of claim 1 wherein the angled bend defined in the body is in the form of a channel having a 90 degree bend.

4. The device of claim 1 further comprising:
   a planar electrode disposed on the upper wall of the body.

5. The device of claim 1 further comprising:
   an analytical device adapted to perform at least one analysis or measurement of particulates collected at the destination location.

6. The device of claim 1 wherein the body further includes at least one lateral side wall extending along the bottom wall, the at least one lateral wall defining a plurality of sample collection ports.

7. The device of claim 1, wherein an additional electrode at the top wall provides a bias field that helps to compact the incoming particulates between the top wall and the fin structure.

8. A bio-enrichment device comprising:
   a cell body defining an inlet, an outlet, an inlet wall, a collection wall opposite from the inlet wall, a bottom wall extending between the inlet wall and the collection wall, disposed orthogonally to the outlet, and a top wall extending between the inlet and the outlet and opposite from the bottom wall; the inlet wall, the collection wall, the bottom wall, and the top wall defining an expansion cavity, the inlet wall including downwardly angled bend at the opening of the expansion cavity, said opening configured to diffuse a laminar flow medium, a top surface of the inlet wall being in a plane distinct from an upper surface of the bottom wall, the cavity contains a first path adjacent to the inlet and a second path adjacent to the outlet, each with a first height, and the expansion cavity with a height larger than the first height to connect the inlet and the outlet via the first path and the second path, wherein the height difference permits for a slowing down of the laminar flow medium;
   a first traveling wave grid disposed on the bottom wall;
   a second traveling wave grid extending along the collection wall;
   the cell body further defining at least one sample collection port at a region proximate one of the first traveling wave grid and the second traveling wave grid, wherein upon operation of the device and admittance of the laminar flowing medium contains bio-agents dispersed therein to the inlet defined in the body, bio-agents are collected at the at least one sample collection port; and
   a fin extending within the expansion chamber positioned in relation to the top wall of the expansion chamber, such that the initial dispersion of the bio-agents is compacted by forcing at least a majority of the bio-agents to travel between the top wall and a top side of the fin upon entering the expansion cavity, where the fin is generally elongated along a direction of the laminar flow.

9. The bio-enrichment device of claim 8 wherein the first and second traveling wave grids are oriented perpendicular to each other.

10. The bio-enrichment device of claim 8 wherein the concentration of bio-agents in the medium as measured at the at least one sample collection port is greater than the concentration of bio-agents in medium as measured at the inlet of the body, by a factor of about 100 to about 1000.

11. The bio-enrichment device of claim 8 wherein the inlet includes an angled bend of about 90 degrees.

12. The bio-enrichment device of claim 8 wherein the expansion cavity includes only a recessed region.

13. The bio-enrichment device of claim 8 further comprising a planar electrode disposed on the top wall.

14. The bio-enrichment device of claim 8 wherein the cell achieves generally laminar flow within the cells interior with negligible in-plane velocity on the traveling wave grid.

15. The device of claim 8, further including an additional electrode at the top wall configured to provide a bias field between said inlet wall and said top wall that urges said bio agents between said top wall and said top side of the fin.

16. A method for collecting and concentrating bio-agents from a flowing medium, the method comprising:
providing a hybrid flow cell configured to enable incremental processing of a partial volume of the flowing medium including (i) a body defining an inlet, an outlet, opposing bottom and top walls extending at least partially therebetween and defining an expansion cavity, the cavity including a collection wall, disposed orthogonally to the outlet, extending from a downstream region of the bottom wall, the inlet wall including downwardly angled bend, creating an opening into said expansion cavity, said opening configured to diffuse a laminar flow medium, a top surface of the inlet wall being in a plane distinct from an upper surface of the bottom wall, the expansion cavity contains a first path adjacent to the inlet and a second path adjacent to the outlet, each with a first height, and an expansion cavity with a height larger than the first height to connect the inlet and the outlet via the first path and the second path, wherein the height difference expansion cavity height permits for a slowing down of the laminar flow medium and (ii) a traveling wave grid disposed along the bottom wall and adapted to transport particulates proximate to the grid, to a destination location without an impingement of a sample;
introducing the flowing medium containing bio-agents to the inlet of the flow cell, including reducing velocity of the flowing medium by causing the flowing medium to pass over the inlet wall and over a fin extending within the expansion chamber positioned in relation to the top all of the expansion chamber, such that the initial dispersion of the bio-agents is compacted by forcing at least a majority of the bio-agents to travel between the top wall and a top side of the fin upon entering the expansion cavity, wherein the fin is generally elongated along a direction of the laminar flow; and
activating the traveling wave grid disposed on the bottom wall to thereby collect bio-agents from the flowing medium and transport the collected bio-agents to the destination location wherein the collected bio-agents are within a given range of charge to size ratio;
wherein the concentration of bio-agents as measured at the destination location increases by a factor within the range of from about 100 to about 1000 as compared to bio-agents as measured at the inlet.

17. The method of claim 16 wherein the hybrid flow cell further includes (iii) a second traveling wave grid extending along the collection wall, and the destination location to which collected bio-agents are transported is the collection wall, the method further comprising:
activating the second traveling wave grid to thereby transport collected bio-agents to a second destination location.

18. The method of claim 16 wherein total process time is the summation of flow separation ($t_{FFF}$) and concentration ($t_{TW}$) given by:

$$t_{FFF}=h^2/\mu V_{FFF} \text{ and } t_{TW}=LS/\alpha\mu V_{TW}.$$

19. The method of claim 16 further comprising redirecting the bio-agents into a corner for concentration and sequencing the bio-agents into a band.

20. An apparatus for collecting and concentrating a sample dispersed in a flowing medium, said apparatus comprising:
a body including an inlet, an outlet, and an expansion cavity, said expansion cavity including opposing top and bottom walls and a collection wall, disposed orthogonally to the flow within the cavity and extending from a downstream region of the bottom wall, said inlet including a bottom wall with a downwardly angled bend, creating an opening of said expansion cavity with a height about ten times larger than that of the inlet, said opening configured to slow the fluid flow into said expansion cavity;
a traveling wave grid disposed along the bottom wall, comprising at least three phases, each phase comprising a different voltage for transporting particulates within a given charge to size ratio proximate to said grid, to said collection wall; and
a fin extending within the expansion chamber positioned in relation to the top wall of the expansion chamber, such that the initial dispersion of the particulates is compacted by forcing at least a majority of the particulates to travel between the top wall and a top side of the fin upon entering the expansion cavity, where the fin is generally elongated along a direction of the laminar flow.

21. The apparatus of claim 20, wherein said expansion cavity only extends downwardly from said inlet.

22. The apparatus of claim 20, wherein said apparatus includes only a single fin.

* * * * *